(12) United States Patent
Borja et al.

(10) Patent No.: US 9,603,934 B2
(45) Date of Patent: Mar. 28, 2017

(54) ANHYDROUS HYDROGEL COMPOSITION AND DELIVERY SYSTEM

(71) Applicant: Acupac Packaging, Inc., Mahwah, NJ (US)

(72) Inventors: John Borja, Keyport, NJ (US); Stephanie Sharon Hayano, Millerton, NY (US)

(73) Assignee: Acupac Packaging, Inc., Mahwah, NJ (US)

( * ) Notice: Subject to any disclaimer, the term of this patent is extended or adjusted under 35 U.S.C. 154(b) by 0 days.

(21) Appl. No.: 14/280,220

(22) Filed: May 16, 2014

(65) Prior Publication Data

US 2015/0017105 A1  Jan. 15, 2015

Related U.S. Application Data

(60) Provisional application No. 61/824,893, filed on May 17, 2013.

(51) Int. Cl.

| | |
|---|---|
| *A61K 47/38* | (2006.01) |
| *A61K 47/10* | (2006.01) |
| *A61K 8/34* | (2006.01) |
| *A61K 8/73* | (2006.01) |
| *A61K 8/35* | (2006.01) |
| *A61K 39/395* | (2006.01) |
| *A61Q 11/00* | (2006.01) |
| *C07K 14/715* | (2006.01) |
| *C07K 16/24* | (2006.01) |
| *A61K 9/00* | (2006.01) |
| *A61K 9/06* | (2006.01) |
| *A61K 31/122* | (2006.01) |
| *A61K 31/785* | (2006.01) |
| *A61K 33/18* | (2006.01) |
| *A61K 33/38* | (2006.01) |
| *A61Q 19/00* | (2006.01) |
| *A61K 8/02* | (2006.01) |
| *A61K 8/04* | (2006.01) |
| *A61K 38/17* | (2006.01) |
| *A61K 38/18* | (2006.01) |
| *A61K 38/40* | (2006.01) |
| *A61K 39/00* | (2006.01) |

(52) U.S. Cl.
CPC ............ *A61K 47/38* (2013.01); *A61K 8/0216* (2013.01); *A61K 8/042* (2013.01); *A61K 8/345* (2013.01); *A61K 8/355* (2013.01); *A61K 8/731* (2013.01); *A61K 9/006* (2013.01); *A61K 9/06* (2013.01); *A61K 31/122* (2013.01); *A61K 31/785* (2013.01); *A61K 33/18* (2013.01); *A61K 33/38* (2013.01); *A61K 38/1793* (2013.01); *A61K 38/18* (2013.01); *A61K 38/1858* (2013.01); *A61K 38/40* (2013.01); *A61K 39/3955* (2013.01); *A61K 47/10* (2013.01); *A61Q 11/00* (2013.01); *A61Q 19/00* (2013.01); *C07K 14/7151* (2013.01); *C07K 16/241* (2013.01); *A61K 2039/505* (2013.01); *A61K 2800/10* (2013.01); *A61K 2800/31* (2013.01); *A61K 2800/591* (2013.01); *A61K 2800/805* (2013.01); *A61K 2800/81* (2013.01); *A61K 2800/92* (2013.01); *C07K 2317/21* (2013.01); *C07K 2317/76* (2013.01); *C07K 2317/94* (2013.01); *C07K 2319/035* (2013.01); *C07K 2319/32* (2013.01)

(58) Field of Classification Search
USPC .................................................. 424/443, 777
See application file for complete search history.

(56) References Cited

U.S. PATENT DOCUMENTS

| | | |
|---|---|---|
| 4,418,057 A | 11/1983 | Groat et al. |
| 5,462,749 A | 10/1995 | Rencher |
| 5,718,886 A | 2/1998 | Pellico |
| 6,399,091 B1 * | 6/2002 | Berthold et al. ............ 424/443 |
| 2002/0098155 A1 * | 7/2002 | Dodd et al. ................... 424/49 |
| 2003/0232895 A1 | 12/2003 | Omidian et al. |
| 2006/0110482 A1 * | 5/2006 | Levine et al. ................ 424/777 |
| 2010/0062048 A1 | 3/2010 | Hsia et al. |

OTHER PUBLICATIONS

International Search Report and Written Opinion received for International Patent Application No. PCT/US2014/38451, dated Mar. 9, 2015, 7 pages.
International Preliminary Report on Patentability for application No. PCT/US2014/038451, mailed Nov. 26, 2015, 4 pages.
Karl Fisher Experimental Analysis, Anhydrous Gel, Analyst Diane Reed, dated Dec. 28, 2015, 1 page.

* cited by examiner

*Primary Examiner* — Walter Webb
(74) *Attorney, Agent, or Firm* — Ziegler IP Law Group, LLC

(57) ABSTRACT

The present disclosure relates to anhydrous hydrogels useful as mucoadhesive (oral compositions) or as topical agents and may be used to deliver an active agent such as active pharmaceutical agents (API's), coagulants, fragrances, flavors, and other actives and excipients.

6 Claims, No Drawings

ANHYDROUS HYDROGEL COMPOSITION AND DELIVERY SYSTEM

FIELD

The aspects of the present disclosure relates to anhydrous hydrogels useful as mucoadhesive (oral compositions) or as topical agents and may be used to deliver an active agent such as active pharmaceutical agents (API's), coagulants, fragrances, flavors, and other actives and excipients.

BACKGROUND

Hydrogels refer to a network of hydrophilic polymer chains that are generally found as a colloidal gel in which water is the dispersion medium. Hydrogels are highly absorbent (they can contain over 99.9% water) natural or synthetic polymers. Hydrogels also possess a degree of flexibility very similar to natural tissue, due to their significant water content ("Terminology of polymers and polymerization processes in dispersed systems (IUPAC Recommendations 2011)". Pure and Applied Chemistry 83 (12): 2229-2259. 2011). Common uses for hydrogels include: tissue engineering, sustained-release drug delivery systems, sensors (including biosensors), disposable diapers or sanitary napkins, contact lenses, and dressings for healing of burn or other wounds.

Hydrogels are characterized by the inclusion of water which acts to disperse the polymer into a colloidal mass. Unfortunately, the presence of water limits the utility of these products to water sensitive materials or environments where moisture is contraindicated. The physical properties of water also dictate the physical properties of the hydrogel, such as reactivity to acids and bases. Thus there is a need to identify new hydrogels without the aqueous limitations.

SUMMARY

The aspects of the present disclosure relate to an anhydrous hydrogel for the delivery of an active agent(s). Particularly important active agents are those that are moisture sensitive. The aspects of the present disclosure also relate to processes for the preparation of, intermediates used in the preparation of, compositions (e.g., pharmaceutical, medical device cosmetic, industrial) containing and the uses of such hydrogels in the treatment of disorders or application of specified agents to a surface.

One specific embodiment of the present disclosure relates to compositions comprising an active agent (including acceptable salt thereof) pharmaceutical composition. Accordingly, in one embodiment, the present disclosure relates to a pharmaceutical composition comprising an active agent, a pharmaceutically acceptable carrier and, optionally, additional medicinal or pharmaceutical agent(s).

Hydrogels are formed by combining a biocompatible polymer with a polyalcohol followed by the addition of an energy source such as heat or radiation. The hydrogels of the present disclosure do not dry out or change shape upon standing. They are also resistant to so called "cold creep" upon standing.

Suitable biocompatible polymers include sodium carboxymethylcellulose, pectin, sodium alginate, sodium/calcium alginate, polylactic acid, chitosan, carageenan, xanthan, gellan, polyaspartic acid, polyglutamic acid, hyaluronic acid or salts or derivatives thereof. Most preferred is sodium carboxymethylcellulose.

Polyalcohols include alcohols containing 2 to 10 carbon atoms and 2 to 7 hydroxyl groups including ethylene glycol, 1,2-propylene glycol, 1,4-butylene glycol, glycerine, erythrit (meso-1,2,3,4-Butantetrol), sorbit, mannit, methylglucoside, diglycerine, triglycerine and/or pentaerythrit. Particularly, the polyol is glycerin.

Active agents include pharmaceutical agents such as analgesics, decongestants, bronchodilators and other antiasthmatic agents, cardiovascular agents such as beta-blockers, ACE inhibitors, diuretics, antithrombics, etc., diabetic agents, antihistamines, anesthetics, antifungals, antinauseants, antiemetics, antibacterial agents, antifungal agents, corticosteroids, neurological agents, anti-inflammatories, vaccines, biological agents (such as Humera, Enbrel and Remicade), wound healing agents and anticonvulsants. Vitamins (particularly A, C, D and E) are a particular embodiment of an active agent. The concentration of the active ingredient in the gel base is, of course, dependent on the identity of the active agent, the condition and patient being treated and the potency desired.

One group of particularly interesting active agents include pharmaceutical agents that are moisture sensitive such as biologicals, enzymes, proteins (and fragments thereof). Other moisture sensitive pharmaceutical agents include Adderall, alprazolam, gemifloxacin, hydromorphone and zolmitriptan.

Another embodiment relates to antifungal active agents such as Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, and Micafungin.

Another embodiment of the present disclosure relates to wart removal compounds such as salicylic acids. Such treatments are of specific interest due to heightened response to the anhydrous medium of the hydrogel.

One specific embodiment relates to wound healing agents and products (such as gauze, bandage, and synthetic skin). Such agents include aloe, benzyl alcohol, coagulants (such as styptic, chitosan, vitamin K, phytomenadione, menadione, etamsylate, carbazochrome Batroxobin), ferric sulfate, ticosan, becaplermin, antimicrobial agents (including antibiotics such as gentamycin, polymyxin B, zinc bacitracin, metronidazole, ofloxacin, minocycline, hydrocortisone, triamcinolone and tetracycline), antifungals, silver, povidone-iodine, polyhexamethylene biguanide, dialkylcarbamoyl-chloride, lactoferrin, growth factors (such as epidermal growth factor (EGF), platelet derived growth factor (PDGF), fibroblast growth factor (FGF), transforming growth factor (TGF-b1), insulin-like growth factor (IGF-1), human growth hormone, granulocyte macrophage colony stimulating (GM-CSF)).

Another embodiment relates to scar healing agents such as vitamins, aloe vera, and benzyl alcohol.

Another embodiment of the present disclosure relates to active agents of hemp oils, particularly CDB (or cannabidiol) and THC (tetrahydrocannabinol).

Active agents also includes cosmetic agents such as caffeine, sunscreens (such as butyl methoxydibenzoylmethane, oxybenzone, bumetrizole, ecamsule, phenylbenzimidazole sulfonic acid, ethylhexyl methoxycinnamate, menthyl anthranilate, octocrylene, para-aminobenzoic acid (PABA), and Tinosorb M), anti-inflammatories (such as salicylates), anti-acne agents (such as (isotretinoin, Benzamycin, clindamycin, Erythromycin, minocycline and tretinoin), vitamins (particularly vitamins C and E, Biotin), ubiquinone, retinoids, Minoxidyl, Zinc pyrithion, ketoconazole, allantoin, herbal extracts (such as Passion Fruit extract (Passiflora Edulis), Red rose extract, Raspberry extract (Rubus Idaeus), Yucca herbal extract, Aloe vera leaf gel, Tea tree oil (Melaleuca Alternifolia), Peppermint leaf oil, Spearmint leaf oil, Wintergreen leaf oil (Gaultheria Procumbens), Lavender oil, Cinnamon leaf oil, Lemon peel oil, Valencia orange peel oil, Pink grapefruit peel oil, Roman chamomile oil (Anthemis Nobilis Flower Oil), and Jasmine oil), protein hydrolysates (i.e. short protein fragments that are still called "peptides") and skin lightening agents.

One particular cosmetic agent of interest is coenzyme Q10 (Co Q10), also known as ubiquinone, ubidecarenone, coenzyme Q, and abbreviated at times to CoQ10, CoQ, or Q10. Ubiquinone is a 1,4-benzoquinone, where Q refers to the quinone chemical group, and 10 refers to the number of isoprenyl chemical subunits in its tail.

Active agents also includes breath fresheners and oral hygienics such as triclosan, chlorhexidine gluconate and complexed metals such as Ag, Cu, Zn or Sn. Dental adhesives such as Gantrez MS-955 polymer (a mixed sodium and calcium salt of methyl vinyl ether and maleic anhydride copolymer supplied as a powder) are also active agents. The formulations of the present disclosure are particularly suitable as dental adhesives demonstrating significant holding power over other adhesive technologies. The formulations of the present disclosure are also useful in the treatment of dry mouth and dry vagina syndromes.

Active agents also include odor reducing agents such as cyclodextrins, sodium bicarbonate, activated charcoal, potassium bicarbonate, zinc undecylenate, undecylenic acid methyl ester, chlorophyll copper complex (CCC), Grillocin, bismuth compounds such as bismuth salicylate (BiS), bismuth subgallate (BiG) and bismuth citrate (BiC), and esters of 3-methyl-2-hexenoic acid.

The hydrogels of the present disclosure are also useful ingredients in disposable diapers and feminine napkins. Ostomy bags and devices are also important products benefiting from the odor reduction properties of the present hydrogels.

The hydrogels of the present disclosure are also useful for treatment of nipple disorders, delivery of laxatives and anti-diarrheas such as loperamide and bismuth subsalicylate (such as Kaopectate and Pepto-Bismol).

The hydrogels of the present disclosure are also useful as food additives which can preserve flavor and aroma.

Flavors and fragrances are well known in the food and cosmetic industry. Many of these compounds are susceptible to hydrolytic deactivation. Formulations of such flavor and fragrance compounds in the hydrogels of the present disclosure have surprising shelf life and release kinetics.

The formulations of the present disclosure are also useful sensors, electrodes and circuits. The use of these hydrogels in defibrillators is advantageous due to the resilience of the actives in a non-aqueous base.

The formulations of the present disclosure are also useful in the field of veterinary medicine for the administration of active agents to pets and farm animals.

The formulations of the present disclosure are also useful as diagnostic tools for the identification of infection, metal contamination and humidity.

Another embodiment of the present disclosure relates to compositions used as a rheology modifier for gel and liquid formulations.

A preferred embodiment of the present disclosure relates to an anhydrous hydrogel composition comprising anhydrous glycerin, anhydrous sodium carboxymethyl cellulose and an active agent.

Glycerin (also commonly known as glycerol, glycerine, propanetriol and 1,2,3-trihydroxypropane) is a widely used commercial product with over a million tons produced annually. High purity glycerin (>99.5%) is known. Anhydrous glycerin refers to glycerin with minimal residual water. United States Pharmacopeia (USP) describes one recognized standard of high purity anhydrous glycerin (>99.0-101.0%) as containing not more than 0.5% water. The otic therapeutic Auralgan is described as containing USP glycerin with not more than 0.6% water. The present disclosure includes such glycerin containing 0.5% and lower residual water. Specific embodiments include 99.7% (weight) water free, 99.8%, 99.9% and absolute (100%) (i.e. less than 0.3%, 0.2%, 0.1% residual water).

Sodium carboxymethyl cellulose is a cellulose derivative with carboxymethyl groups ($-CH_2-CO_2H$) bound to some of the hydroxyl groups of the glucopyranose monomers that make up the cellulose backbone. Commercial polymer products are typically categorized by average glucopyranose chain length molecular weights (MW) of 70,000, 80,000, 90,000 g/m. Anhydrous sodium carboxymethyl cellulose refers to a product with minimal residual water.

The present inventors have surprisingly found that the combination of anhydrous glycerin and sodium carboxymethyl cellulose (CMC) yields an anhydrous material that upon addition of heat (or radiation) is transformed into an anhydrous hydrogel. Unit dosage formulations may be prepared by the addition of 0.1 mg to 1 g of active agent (depending on the active agent) with glycerin and CMC is likewise transformed into a homogeneous hydrogel upon the addition of heat. These products have less than 0.5% water, more preferably less than 0.4% water, more preferably less than 0.3% water.

Such anhydrous hydrogels are hygroscopic and thus may be subject to post production processes that maintain the product in a water-free state. One such method is coating of the hydrogel with a hydrophobic layer. Alternate methods include storage of products in moisture free containers. Many of the products once formed may be stable enough to atmospheric moisture such that they can be stored in standard delivery apparatus.

Hydrogels of the present disclosure can be subjected to crosslinking methods which enhance the structure and function of the hydrogel. Suitable crosslinking chemical agents include divalent/multivalent metallic cations (e.g., calcium, magnesium, zinc, copper, barium, iron, aluminium, chromium, cerium), phosphates (e.g., pentasodium tripolyphosphate (TPP)), chromates (e.g., dipotassium dichromate), borates (e.g., sodium tetraborate decahydrate), peroxides (e.g., t-butyl hydroperoxide), glycidyl(meth)acrylate, ethylene glycol diglycidyl ether, glutaraldehyde, glycerin, glycols, polyamidoamine epichlorohydrin resin, TMPTA, and the like, and mixtures thereof. Representative crosslinking methods include thermogelation, ionotropic gelation, cryogelation, radiation-induced gelation, chemical gelation, coagulation, crystallization, vulcanization, curing, and combinations thereof.

Another embodiment of the present disclosure relates to anhydrous hydrogels additionally comprising multivalent metal ions (i.e. Ca++, Mg++, Fe+++, Zn++ etc) which may be used to modify the cohesive and solubility characteristics as desired. So-called cross-linking resulting from multivalency makes the products more viscous and less hydrophilic.

Additional excipients include fillers such as fumed silica, calcium carbonate, talc, corns starch, clays, methacrylate powder, polyethylene/polypropylene beads, etc.

The anhydrous hydrogels of the present disclosure may further comprise a buffer such as an acid such as citric acid, benzoic acid, salicylic acid, etc.; neutral buffers such as phosphate buffered saline etc.; or alkaline buffers such as borates etc. These buffering agents may be used to adjust for pH sensitive applications.

In a preferable embodiment of the present disclosure, the hydrogel comprises the biocompatible polymer (CMC) in an amount of 1 to about 50 wt %, the polyalcohol (Glycerin) in an amount of 1 to about 20 wt %, and the active agent is a medicinal herb extract in an amount of 1 to about 30 wt % (unit dosage amounts include 0.1 mg to 1 g, more preferably 50 mg to 750 mg of active).

The anhydrous hydrogels of the present disclosure generally comprise 0.1-50% (w/w) of an anhydrous carboxymethyl cellulose such as carboxymethyl cellulose, 99.5-50% anhydrous glycerin (w/w). and 0.1-50% of an active agent.

Another embodiment of the present disclosure relates to an anhydrous hydrogel comprising from 5-30% NaCMC, 95-70% anhydrous glycerin and 0.1-30% active agent.

Another embodiment of the present disclosure relates to an anhydrous hydrogel comprising from 10-20% NaCMC, 90-80% anhydrous glycerin and 0.1-30% active agent.

Another embodiment of the present disclosure relates to an anhydrous hydrogel comprising from 14-16% NaCMC, 86-84% anhydrous glycerin and 0.1-30% active agent.

Another embodiment of the present disclosure relates to a composition of any of the aforesaid embodiments of hydrogel wherein said composition is in thin film, tablet, capsule, oral solution, or oral suspension dosage form.

Formulations suitable for oral administration include solid, semi-solid and liquid systems such as soft or hard capsules containing multi- or nano-particulates, liquids, or powders; lozenges (including liquid-filled); chews; gels; fast dispersing dosage forms; films; ovules; sprays; and buccal/mucoadhesive patches.

The hydrogels of the present disclosure may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Another embodiment of the present disclosure relates to an oral pharmaceutical preparation containing a therapeutically effective amount of an active agent or a salt thereof for once daily administration.

Another embodiment of the present disclosure relates to a composition containing particles which have a core containing an active agent or a salt thereof coated with a barrier layer. The barrier layer is formed from a coating liquid that contains a least one water insoluble barrier forming component selected from a group consisting of ethyl cellulose, copolymers of acrylic and methacrylic esters and natural or synthetic waxes, and a plasticizer.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a subject.

Administration of the compounds of Formula I may be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active agent administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of an active agent together with an at least one additional pharmaceutical or medicinal agent, either sequentially or simultaneously.

The present disclosure includes the use of a combination of an active agent and one or more additional pharmaceutically active agent(s). If a combination of active agents is administered, then they may be administered sequentially or simultaneously, in separate dosage forms or combined in a single dosage form. Accordingly, the present disclosure also includes pharmaceutical compositions comprising an amount of: (a) a first agent comprising an active agent or a pharmaceutically acceptable salt of the compound; (b) a second pharmaceutically active agent; and (c) a pharmaceutically acceptable carrier, vehicle or diluent.

In a further embodiment, a kit is disclosed. One example of such a kit is a kit including an injectable composition of a hydrogel. Another kit embodiment is a thin film adhesive.

These and other aspects and advantages of the exemplary embodiments will become apparent from the following detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

DETAILED DESCRIPTION OF THE PRESENT DISCLOSURE

The manufacture of the anhydrous hydrogels may be achieved using a coating line with a heat tunnel, coating a mixture of glycerin (anhydrous) with NaCMC (anhydrous) to a desired thickness and passing the mixture through an oven (under suitable dry conditions so as to retain water free atmosphere) at 105° C. (min) for about 5 minutes (min) until mixture sets. The product may be extruded into molds or thin films. Active agents and additional components are either anhydrous or dehydrated before use. Subject mixture is treated to the same processing parameters as the coating line.

Preferably the composition is extruded directly onto a substrate such as a backing layer or release liner, and then pressed. The thickness of the resulting hydrogel-containing film, for most purposes, will be in the range of about 0.20 mm to about 0.80 mm, more usually in the range of about 0.37 mm to about 0.47 mm.

The hydrogel compositions of the present disclosure may be prepared by solution casting, by admixing the glycerin and CMC at a concentration typically in the range of about 35% to 60% w/w followed by the addition of heat or radiation. The resulting solution is cast onto a substrate such as a backing layer or release liner. Both admixture and casting are preferably carried out at as low temperature as permitted. The substrate coated with the hydrogel film is then baked at a temperature in the range of about 80 degree C. to about 100 degree C., optimally about 90 degree C., for time period in the range of about one to four hours, optimally about two hours.

An active agent may be delivered to a body surface by simply placing a hydrogel composition of the present disclosure on a body surface in active agent-transmitting relation thereto. Alternatively, an active agent-containing hydrogel composition may be incorporated into a delivery system or "patch." In manufacturing such systems, the hydrogel adhesive composition may be cast or extruded onto a backing layer or release liner and will serve as the skin-contacting face of the system and act as an active agent reservoir. Alternatively, the hydrogel composition may be used as an active agent reservoir within the interior of such a system, with a conventional skin contact adhesive laminated thereto to affix the system to a patient's body surface.

Optional ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the present disclosure are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the present disclosure may be adapted from those described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release may be adapted from those described in WO 00/35298.

Systems for the topical, transdermal or transmucosal administration of an active agent may comprise: a reservoir containing a therapeutically effective amount of an active agent; an adhesive means for maintaining the system in active agent transmitting relationship to a body surface; and a backing layer as described above, wherein a disposable release liner covers the otherwise exposed surface, protecting such surface during storage and prior to use (also as described above).

The composition will contain a quantity of an active agent effective to provide the desired dosage or effect over a predetermined delivery period.

The compositions of the present disclosure may also include a rate-controlling membrane on the body surface side of the drug reservoir. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

The compositions of the present disclosure may also serve to deliver an active agent using other routes of administration. For example, the compositions may be formulated with excipients, carriers and the like suitable for oral administration of an orally active drug. The compositions may also be used in buccal and sublingual drug delivery, insofar as the compositions can adhere well to moist surfaces within the mouth. In buccal and sublingual systems, hydrolyzable and/or bioerodible polymers may be incorporated into the compositions to facilitate gradual erosion throughout a drug delivery period. Still other types of formulations and drug delivery platforms may be prepared using the present compositions, including implants, rectally administrable compositions, vaginally administrable compositions, and the like.

Example 1

Using methods analogous to those described above the following anhydrous formulations were prepared.

| Odor Control | | | |
|---|---|---|---|
| Description | A | B | C |
| Glycerin (99.7%) | 78.0 | 77.0 | 78.0 |
| Sodium CMC | 10.0 | 9.8 | 9.8 |
| Zinc Oxide | 0.0 | 0.8 | 0.8 |
| Magnesium Oxide | 0.0 | 0.5 | 0.5 |
| PEG-40 HCO | 10.0 | 10.0 | 10.0 |
| Undecylenic Acid Methyl Ester | 0.5 | 0.5 | 1.0 |
| Fragrance | 1.5 | 1.5 | 0.0 |
| Total | 100.0 | 100.0 | 100.0 |

Example 2

| Dry Mouth | | | |
|---|---|---|---|
| Description | A | B | C |
| Glycerin (99.7%) | 74.00 | 78.00 | 78.00 |
| Sodium CMC | 18.00 | q.s. | q.s. |
| Coconut Oil (for example) | 7.80 | 5.00 | 5.00 |
| CoQ10 | 0.20 | 0.00 | 0.00 |
| Flouride compound | 0.00 | 0.25-1.00 | 0.25-1.00 |
| Flavor | trace | trace | trace |
| Total | 100.0 | 100.0 | 100.0 |

Example 3

| Food Thickener/Gravy | | | |
|---|---|---|---|
| Description | A | B | C |
| Glycerin (99.7%) | 69.00 | 70.00 | 75.00 |
| Sodium CMC | 20.00 | 20.00 | 20.00 |
| Anhydrous Coconut Oil | 6.00 | 5.00 | 5.00 |
| Dehydrated Chicken Flavor | 5.00 | 0.00 | 0.00 |
| Dehydrated Beef Flavor | 0.00 | 5.00 | 0.00 |
| Total | 100.0 | 100.0 | 100.0 |

Example 4

| Denture Fixative Gel Film | | | | | |
|---|---|---|---|---|---|
| Description | A | B | C | D | E |
| Glycerin (99.7%) | q.s. | q.s. | q.s. | q.s. | q.s. |
| Sodium CMC | 20.00 | 20.00 | 20.00 | 20.00 | 20.00 |
| Ca(OH)$_2$ | 0.140-2.54 | | | | 0.140-2.54 |
| Mg(OH)$_2$ | | 0.100-1.82 | | | 0.100-1.82 |
| Zn(OH)$_2$ | | | 0.180-3.40 | | 0.180-3.40 |
| Trivalent cmpd.* | | | | trace | 0.00-trace |
| Total | 100.00 | 100.00 | 100.00 | 100.00 | 100.00 |

Example 5

| API | | |
|---|---|---|
| Description | A | C |
| Glycerin (99.7%) | 78.00 | 80.00 |
| Sodium CMC | 17.00 | 20.00 |
| anhydrous Coconut Oil (for example) | 5.00 | 0.00 |
| API (e.g., etanercept) | 0.001-5.00% | 0.001-5.00% |
| Flavor | trace | trace |
| Total | 100.0 | 100.0 |

Example 6

| Polymer-Polymer Complex Denture Adhesive Anhydrous Gel | | | | |
|---|---|---|---|---|
| Description | A | B | C | D |
| Glycerin (99.7%) | q.s. | q.s. | q.s. | q.s. |
| Sodium CMC | 20.00-50.00 | 20.00-50.00 | 20.00-50.00 | 20.00-50.00 |
| Gantrez MS-955 (Ca—Na Salt) | 1.00-30.00 | | | |
| Polyvinylpyrrolidinone (PVP) K90 (anhydrous) | | 1.00-20.00 | | |
| Polyox 301(anhydrous) | | | 1.00-15.00 | |
| Polyvinyl alcohol (PVOH) (anhydrous) | | | | 1.00-20.00 |
| TOTAL | 100.00 | 100.00 | 100.00 | 100.00 |

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. An anhydrous hydrogel product obtained by the process of combining from 5-30% by weight NaCMC with minimal residual water, 95-70% by weight anhydrous glycerin containing 0.5% or lower residual water, 0.1-30% by weight dehydrated active agent, and followed by the addition of an energy source.

2. An anhydrous hydrogel obtained by the process of combining wherein said anhydrous hydrogel comprises from 10-20% by weight NaCMC with minimal residual water, 90-80% by weight anhydrous glycerin containing 0.5% or lower residual water, 0.1-30% by weight dehydrated active agent, and followed by the addition of an energy source.

3. An anhydrous hydrogel obtained by the process of combining from 14-16% by weight NaCMC with minimal residual water, 86-84% by weight anhydrous glycerin containing 0.5% or lower residual water, 0.1-30% by weight dehydrated active agent, and followed by the addition of an energy source.

4. An anhydrous hydrogel product according to claim 1 wherein the energy source is heat or radiation.

5. An anhydrous hydrogel product according to claim 2 wherein the energy source is heat or radiation.

6. An anhydrous hydrogel product according to claim 3 wherein the energy source is heat or radiation.

\* \* \* \* \*